(12) United States Patent
Soulie et al.

(10) Patent No.: US 9,427,486 B2
(45) Date of Patent: Aug. 30, 2016

(54) FILTER CARTRIDGE FOR AN AIR PURIFIER

(71) Applicants: SEB S.A., Ecully (FR); ETHERA, Grenoble (FR)

(72) Inventors: Jean-Pierre Soulie, Vernon (FR); Eric Marchal, Houlbec-Cocherel (FR); Yves Bigay, Saint-Ismier (FR); Emmanuel Chevallier, Gif-sur-Yvette (FR)

(73) Assignees: SEB S.A., Ecully (FR); ETHERA, Grenoble (FR)

( * ) Notice: Subject to any disclaimer, the term of this patent is extended or adjusted under 35 U.S.C. 154(b) by 252 days.

(21) Appl. No.: 14/317,719

(22) Filed: Jun. 27, 2014

(65) Prior Publication Data

US 2015/0004065 A1    Jan. 1, 2015

(30) Foreign Application Priority Data

Jun. 28, 2013    (FR) ..................... 13 56322

(51) Int. Cl.
| | |
|---|---|
| *A61L 9/00* | (2006.01) |
| *B01D 53/02* | (2006.01) |
| *B01J 20/32* | (2006.01) |
| *B01D 53/72* | (2006.01) |
| *B01D 53/82* | (2006.01) |
| *B01J 20/18* | (2006.01) |
| *B01J 20/20* | (2006.01) |
| *B01D 53/04* | (2006.01) |
| *B01J 20/28* | (2006.01) |

(52) U.S. Cl.
CPC ............... *A61L 9/00* (2013.01); *B01D 53/02* (2013.01); *B01D 53/72* (2013.01); *B01D 53/82* (2013.01); *B01J 20/18* (2013.01); *B01J 20/20* (2013.01); *B01J 20/28045* (2013.01); *B01J 20/28052* (2013.01); *B01J 20/3204* (2013.01); *B01J 20/3251* (2013.01); *B01J 20/3253* (2013.01); *B01J 20/3255* (2013.01); *B01D 53/0415* (2013.01); *B01D 2251/21* (2013.01); *B01D 2251/80* (2013.01); *B01D 2253/102* (2013.01); *B01D 2253/108* (2013.01); *B01D 2253/1124* (2013.01); *B01D 2253/202* (2013.01); *B01D 2257/708* (2013.01); *B01D 2257/7027* (2013.01); *B01D 2259/4143* (2013.01); *B01D 2259/4145* (2013.01); *B01D 2259/4508* (2013.01); *B01J 20/28057* (2013.01); *B01J 2220/62* (2013.01)

(58) Field of Classification Search
CPC ........................................................ A61L 9/00
See application file for complete search history.

(56) References Cited

U.S. PATENT DOCUMENTS

| | | |
|---|---|---|
| 5,522,808 A | 6/1996 | Skalla |
| 8,173,440 B2 | 5/2012 | Paolacci et al. |

FOREIGN PATENT DOCUMENTS

| | | |
|---|---|---|
| DE | 10155879 A1 | 6/2003 |
| FR | 2890745 A1 | 3/2007 |
| JP | 2010022979 A | 2/2010 |

*Primary Examiner* — Sean E Conley
(74) *Attorney, Agent, or Firm* — The Webb Law Firm

(57) ABSTRACT

Provided is a filter cartridge for an air purifier, comprising a structure ensuring the retention of a filter medium, the filter medium comprising a standard absorbent material chosen from the group consisting of activated charcoal or zeolites, and the filter medium further comprises a nanoporous specific absorbent material functionalized with probe molecules in such a way that chemical pollutants of the aldehyde type can be trapped.

14 Claims, 2 Drawing Sheets

FILTER CARTRIDGE FOR AN AIR PURIFIER

CROSS-REFERENCE TO RELATED APPLICATION

This application claims priority to French Patent Application No. 1356322 filed Jun. 28, 2013, the disclosure of which is hereby incorporated in its entirety by reference.

FIELD OF THE INVENTION

The present invention relates in a general manner to the field of air purifiers, and more particularly to filter cartridges for these kinds of appliances with the capacity to absorb aldehydes and formaldehydes in particular.

DESCRIPTION OF RELATED ART

The term aldehyde denotes any organic molecule having a terminal carbonyl functional group preferably chosen from the group consisting of formaldehyde, acetaldehyde, propionaldehyde, butyraldehyde, acrolein, pentanal, hexanal, and benzaldehyde.

Aldehydes are among the most abundant household chemical pollutants. Their sources are extremely numerous. They may be connected to an outdoor production such as the photo-oxidation of methane. However, the main sources of release of aldehydes are found inside dwellings and are very diverse: resins and adhesives used to manufacture chipboard, particle board, and plywood, urea-formaldehyde insulating foams used as thermal insulation, by injection into walls and partitions, and in textile coverings, wallpaper, paint, leather, etc.

Formaldehyde is also a preservative, a disinfectant, and a desiccant. For these reasons, it is widely used as a solvent in the hospital environment for disinfecting surgical instruments and also in the funeral service industry, where embalming is carried out.

Considering the harmful effects of such chemical pollutants to public health, it appears necessary to ensure the purification of the ambient air in residential buildings by reducing the concentration of aldehydes (and notably formaldehyde) and providing novel decontamination devices.

According to the known prior art, the methods for treating gaseous chemical pollutants present in the air can be classified in 2 categories:

Destruction of the pollutant by degradation of the organic compounds until complete mineralization, i.e., until they are transformed into $CO_2$ and $H_2O$ by oxidation or photo-oxidation.

Trapping by porous absorbent materials that retain, but do not degrade, the pollutants. These materials are zeolite or activated charcoal materials and they are commonly used in air treatment for trapping volatile organic compounds and odors.

The first category is based on devices utilizing oxidants such as ozone or technologies favoring oxidation such as photocatalysis or plasma.

The second category utilizes the absorbencies and absorption capacities of porous materials with large specific surface areas (>100 $m^2/g$); the molecules are retained on a porous medium but not degraded.

The first category has the disadvantages of being complex and relatively expensive. Furthermore, it can generate secondary decomposition products that may turn out to be more hazardous than the eliminated compound.

The second category has the drawback of having trapping rates that vary greatly from one chemical compound to be eliminated to another. For example, activated charcoal is sufficiently effective for absorbing aromatic compounds but quite ineffective for absorbing aldehydes and in particular formaldehyde.

The manufacturers of absorbent materials endeavor to improve the absorbency of their materials by functionalizing them. Unfortunately, this functionalization is achieved by impregnation which, if done in sufficient quantity, has the disadvantage of stopping up the pores and thus limiting the trapping capacities.

SUMMARY OF THE INVENTION

The object of the invention is to improve the performances of filter cartridges for air purifiers by adding a medium that absorbs polluting chemical compounds from the air, with regard to substances for which the current absorbent materials are not effective, in particular aldehydes and notably formaldehyde. The filter cartridge thus configured permanently traps the vast majority of all atmospheric pollutants in large quantities.

This object is achieved with a filter cartridge for an air purifier, comprising a structure ensuring the retention of a filter medium, the filter medium comprising a standard absorbent material chosen from the group consisting of activated charcoal or zeolites, characterized in that the filter medium further comprises a specific absorbent nanoporous material functionalized with probe molecules in such a way that chemical pollutants of the aldehyde type can be trapped.

According to another alternative embodiment, the specific absorbent material is manufactured by sol-gel for incorporation in a nanoporous structure of metal oxides of probe molecules capable of trapping aldehydes.

According to another alternative embodiment, the probe molecule bearing a functional group capable of reacting with an aldehyde group is chosen from the group consisting of enaminones and corresponding β-diketone/amine pairs, imines, and hydrazines, or salts derived from these compounds.

According to another alternative embodiment, the structure ensuring the retention of the filter medium is a rigid alveolar structure, the alveoli containing the filter medium.

According to another alternative embodiment, a microperforated film is assembled on the upstream and downstream faces of the rigid alveolar structure.

According to another alternative embodiment, the filling rate of the alveoli with filter medium is greater than 40%.

According to another alternative embodiment, the specific absorbent material is in the form of granules, the dimensions of which range between 0.8 and 2 mm.

According to another alternative embodiment, the shape of the granules is cylindrical, with a ratio L/D≫1, wherein L corresponds to the length of a granule and D corresponds to the diameter of a granule.

According to another alternative embodiment, the structure ensuring the retention of the filter medium is an assembly of several films on which the standard absorbent material and the specific absorbent material are impregnated/sprinkled.

According to another alternative embodiment, the weight of the specific absorbent material represents between 5 and 95% of the weight of the standard absorbent material.

According to another alternative embodiment, the specific surface area of the specific absorbent material ranges between 600 and 1200 $m^2 g$.

The invention also relates to an air purifier comprising a filter cartridge as defined above.

BRIEF DESCRIPTION OF THE DRAWINGS

Other features and advantages of the present invention will emerge more clearly from reading the following detailed description of embodiments of the invention, which are given as not in any way limiting examples and which are illustrated in the appended drawings, wherein.

DETAILED DESCRIPTION OF THE INVENTION

The invention essentially consists of a filter cartridge comprising a filter medium. The filter medium comprises one or several beds of absorbent materials, combined or separated, making it possible to eliminate the volatile organic compounds present in the indoor air by absorption. According to the invention, the absorbed volatile organic compounds are notably aldehydes and/or solvents. The filter cartridge is designed to be introduced into an appliance for purifying the ambient air capable of functioning at flow rates of a few m³/h to several thousand m³/h.

Figure 1:
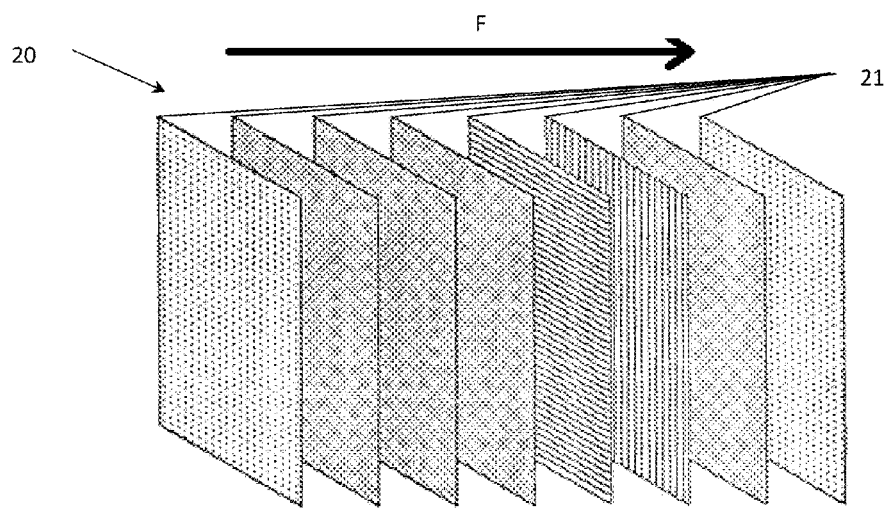
FIG. 1 schematically illustrates a first filter cartridge structure of the invention.
Figure 2A:
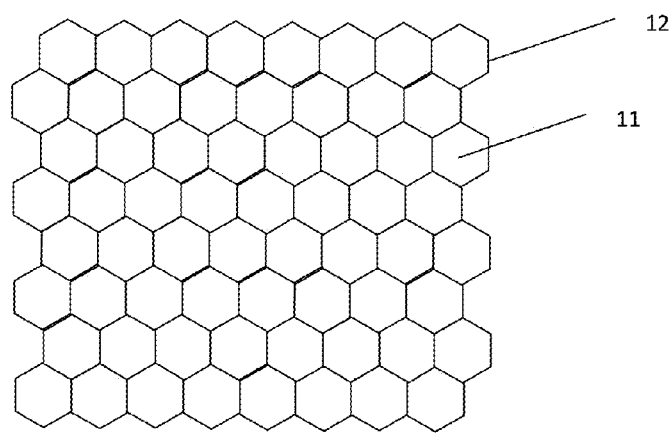
FIGS. 2A and 2B illustrate, respectively, a frontal view and a perspective view of a second filter cartridge structure of the invention.
Figure 2B:
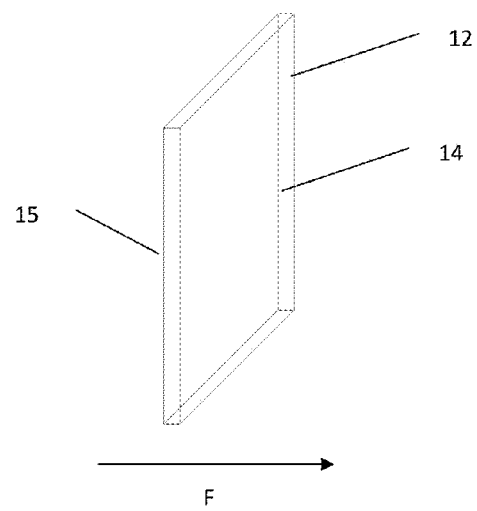

FIGS. 1, 2A, and 2B illustrate examples of filter cartridge structures likely to be used in the scope of the invention.

These structures enable the retention of the filter medium of the invention in the flow of air through the air purifier.

FIG. 1 illustrates a structure 20 (known per se) comprising a series of films 21. In this alternative, the filter medium is impregnated in one or several films 21. All of the films are then assembled (for example, by gluing or welding) in order to form the filter cartridge.

The dimensions and the numbers of films 21 essentially depend upon the desired performances of the air purifier.

According to FIGS. 2A and 2B, the filter cartridge comprises a rigid alveolar structure 12. According to this alternative embodiment, the structure is a honeycomb structure. The filter medium is placed in the alveoli 11 of the structure 12. In order to ensure the retention of the filter medium in the alveoli 11, a micro-perforated film is positioned on the downstream 14 and upstream 15 faces of the rigid alveolar structure 12. The film is, for example, totally permeable to the air flow and does not have any filtration function.

For the two filter cartridge structure alternatives, the cartridge is positioned perpendicular to the air flow F in the air purifier.

The geometry of the filter cartridge of the invention can be in different planar or volume forms. The filter cartridge contains a mixture and/or successive layers of granules containing one or several absorbent materials.

According to the invention, the filter medium comprises a combination of at least one standard absorbent material capable of eliminating a broad spectrum of volatile organic compounds from the indoor air of dwellings and a specific absorbent material for trapping compounds such as aldehydes and more particularly formaldehydes that are not effectively eliminated by the standard absorbent material.

According to the invention, the standard absorbent material is chosen from the group consisting of activated charcoal or the zeolites.

The specific absorbent material is a material capable of specifically trapping a pollutant or a family of pollutants. For example, the filter medium can trap the aldehyde family by means of adapted probe (or active principle) molecules incorporated in a nanoporous structure. An informed choice of probe molecules can allow a more specific trapping of a pollutant such as formaldehyde. The process for manufacturing the specific sol-gel absorbent material allows an introduction of the active principle during its preparation (in situ) and not by impregnation. The process for manufacturing the specific absorbent material makes it possible to introduce a considerable amount of active principle without stopping up the pores because there is no impregnation. The plugging of the pores by impregnation is thus avoided.

Thus by choosing the probe molecule in an appropriate manner, it is possible to eliminate harmful pollutants such as formaldehyde, which the standard absorbent materials are either unable to eliminate or only able to eliminate to a slight degree.

In the case of the sol-gel specific absorbent material, the pollutant reacts with the reactive principle to give rise to a third, less harmful molecule with a higher molecular weight, which will remain trapped in the nanopore network of the specific absorbent material. In contrast to other absorbent materials, this specific absorbent material effects a permanent trapping.

As an example, the specific absorbent material is chosen from the group of materials described in patent application FR2890745, introduced by reference in the present description.

Notably and in a non-limiting manner, the material comprises a sol-gel nanoporous metal oxide matrix, said matrix containing at least one probe molecule bearing at least one functional group capable of reacting with an aldehyde group.

The probe molecule bearing a functional group capable of reacting with an aldehyde group is chosen from the group consisting of enaminones and corresponding β diketone/amine pairs, imines, and hydrazines, or salts derived from these compounds.

Enaminones have the following formula:

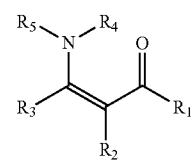

Wherein:

R1 is a hydrogen, an alkyl radical, or an aryl radical,

R2 is a hydrogen,

R3 is a hydrogen, an alkyl radical, or an aryl radical,

R4 is a hydrogen, an alkyl radical, or an aryl radical,

R5 is a hydrogen.

In addition, the β-diketone/amine pair has the following formula:

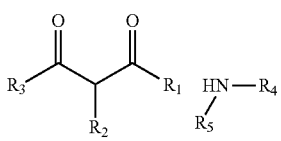

Wherein:
R1 is a hydrogen, an alkyl radical, or an aryl radical,
R2 is a hydrogen,
R3 is a hydrogen, an alkyl radical, or an aryl radical,
R4 is a hydrogen or an alkyl radical,
R5 is a hydrogen or a corresponding salt.

In addition, the imine is a Schiff base chosen from the group consisting of acridine yellow, methyl yellow, or dimethyl yellow.

The hydrazine has the following formula:

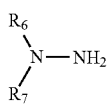

Wherein:
R6 is hydrogen, a C1-C20 alkyl radical, preferably a C1-C10 alkyl radical, more preferably methyl, ethyl, isopropyl, butyl, isobutyl, tert-butyl and pentyl radicals, a C3-C16 aryl radical, notably phenyl and aryl sulfonyl radicals,
R7 is a C3-C16 aryl radical, notably phenyl and aryl sulfonyl radicals.

According to the invention, the sol-gel nanoporous metal oxide matrix is produced from at least one metal oxide with the following formula:

M(X)m(OR8)n(R9)p,

Wherein:
M is a metal chosen from the group consisting of silicon, aluminum, titanium, zirconium, niobium, vanadium, yttrium, and cerium,
R8 and R9 can be either an alkyl radical or an aryl radical,
n, m, and p are whole numbers such that their sum is equal to the valence of M and n is greater than or equal to 2,
X is a halogen.

The specific absorbent material as defined above, which enables the specific trapping of aldehydes and notably formaldehyde, possesses an efficacy in formaldehyde trapping capacity at least 100 times greater than that of activated charcoal dedicated to the total volatile organic compounds and 10 times greater than that of activated charcoal impregnated specifically for trapping gaseous formaldehyde. The permanent trapping capacity of the specific absorbent material is at least 0.01 g of formaldehyde per gram of material. In addition, even when saturated, this specific absorbent material has an adsorption trapping capacity equal to that of activated charcoal impregnated specifically for trapping gaseous formaldehyde.

According to the prior art, activated charcoal or zeolites do not effectively eliminate aldehydes and particularly formaldehyde, whereas this gas is very abundant in indoor air on the one hand and harmful to health on the other. Thus by combining a standard absorbent material and a specific absorbent material, in particular one that is effective for aldehydes and notably formaldehydes, the filter cartridge of the invention enables the elimination not only of aldehydes and in particular formaldehyde owing to the presence of the nanoporous specific absorbent material functionalized with probe molecules, but also of other volatile organic compounds, in particular the family of monocyclic aromatic hydrocarbons (benzene, toluene, ethylene, xylene, etc.) owing to the activated charcoal or the zeolites.

The combination of standard and specific absorbent materials is achieved either by mixing the materials or by combining them in successive mono-material layers.

The standard and specific absorbent materials may be premixed for homogeneous introduction into the filter or they may be introduced separately by sprinkling on several layers or on different levels that are separated physically.

According to the invention, the decontamination/filtration performances of the cartridge are determined notably by the following parameters:
the weight ratio between the standard absorbent material and the specific absorbent material,
the specific surface area of the specific absorbent material,
the shape of the specific absorbent material,
the physical and chemical properties of the standard absorbent material.

The weight ratio between the standard absorbent material and the specific absorbent material can vary by a factor of 95/5 to 5/95: the specific choice is made on the basis of the nature and amount of the pollutants present in the indoor air and the desired performances to be achieved.

As an example, for air containing 20 µg/m$^3$ of formaldehyde and 200 µg/m$^3$ of other volatile organic compounds, preference would be given to using a 10/90 weight ratio of specific absorbent material/activated charcoal. However, it is possible to double, quadruple, etc., the efficacy of the filter medium of the invention by doubling, quadrupling, etc., the amount of specific absorbent material.

Hence in the case of air heavily contaminated with formaldehyde containing, for example, 10 times more formaldehyde than other volatile organic compounds, use would be made of a filter having a 90/10 ratio of specific absorbent material/activated charcoal.

The specific surface area sought for the specific absorbent material is inversely proportional to the size of the pores. Hence the greater the specific surface area, the smaller the size of the pores. Hence in order to have a specific surface area of around 1000 m$^2$/g, the diameter of the pores is typically on the order of nanometers.

Hence the best compromise is sought between a maximum specific surface area for increasing the trapping capacity and efficacy and a limit that must not be exceeded in order to have pores of a size sufficient to allow the pollutants to enter the pores. The target specific surface area range is between 100 and 1500 m$^2$/g, depending on the size of the pollutant molecule to eliminate. For formaldehyde, for example, preference would be given to a range of between 600 and 1200 m$^2$/g.

The granule shape for the specific absorbent material is chosen such that the maximum adsorption surface area (outer surface of the granule) for increasing trapping efficacy is obtained with the least possible pressure drop in order to minimize the energy required for decontamination.

In the case of cylindrical granules, for example, it is known that the adsorption surface area is inversely proportional to the mean diameter of the granules. Hence reducing the granule diameter increases the performances owing to an increase of the trapping surface area. Conversely, this reduction brings about an increase in pressure drop and in energy consumption. Indeed, the bed of granules becomes more compact and therefore less permeable to the air flow passing through it. Granules on the order of millimeters in size (0.2 to 8 mm) typically represent the best compromise between the greatest efficacy and a pressure drop that is not excessive.

Elongated cylinder shapes (i.e., having a ratio L/D>1 (L=length, D=diameter) are of great interest because they are easily produced by molding or extrusion. Their elongated shapes prevent the flat surfaces from adjoining so as not to reduce the adsorption surface area and not to increase pressure drop and energy consumption. In this case, the dimensions (length) on the order of millimeters (0.2 to 8 mm) likewise result in the best compromise.

According to another embodiment, the granules can be in ground form, resulting in particles on the order of millimeters (0.2 to 8 mm) in size. This form is also of interest because for an essentially identical particle diameter, it gives rise to a greater adsorption surface area than would be the case for spherical particles.

Use may also be made of granules smaller than a millimeter provided that use is made of inter-granular (fiber) supports to disperse the granules and reduce pressure drop. In this case films of mixed standard absorbent material/specific absorbent material granules entrapped in fabrics for increasing the surface area of the filter in order to reduce pressure drop are conceivable.

Furthermore, other criteria such as the dimensions of the rigid alveolar structure and the filling rate of the alveoli can also be adjusted in order to obtain the desired performances of the filter cartridge of the invention. Hence the size of the alveoli of the structure is in the range of 1 to 10 times the maximum size of a granule of specific absorbent material. This dimension makes it possible to obtain a good distribution of the granules in the alveoli and to provide for receiving at least 1 granule per alveolus of the rigid alveolar structure.

Similarly, the filling rate of the alveoli with mixtures of standard and specific absorbent materials is, for example, at least 40%. The bulk of the filter cartridge of the invention can thus be limited.

The filter cartridge of the invention does not affect the general prior art design of air purifiers. Indeed, it suffices to insert the filter cartridge of the invention in place of the prior art cartridge. The composition and the features of the filter cartridge of the invention will then be adjusted in relation to the features of the air purifier, notably in relation to the air flow and the dimensions of the cartridge.

Examples of the dimensioning of the filter cartridge of the invention:

The first example is defined for achieving the decontamination of a room having the following features:
volume: 12 m$^3$,
air renewal rate: 5 m$^3$/h,
formaldehyde release rate: 70.6 µg/m$^3$.

The features of the air purifier using the filter cartridge of the invention are as follows:
air flow: 140 m$^3$/h,
alveolar (honeycomb) filter cartridge: width 21 cm, length 53 cm, depth 1 cm (total passage surface area of 0.068 m$^2$),
weight of the specific absorbent material: 20 g.

Figure 3:
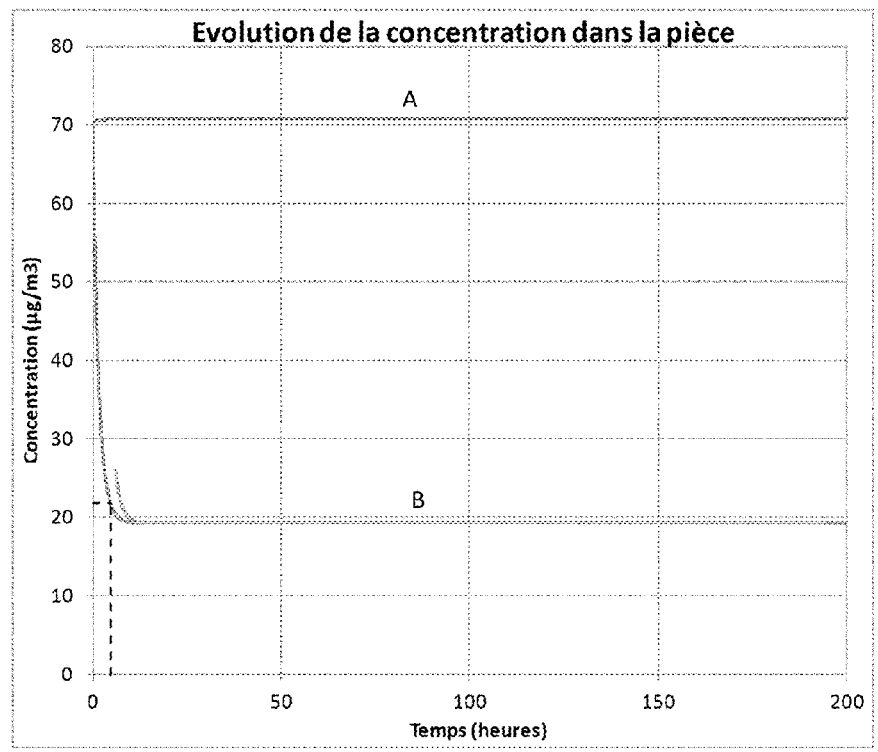
FIG. 3 illustrates the change in the concentration of formaldehyde in a room with a first alternative embodiment of the cartridge of the invention.

The change in the concentration of formaldehyde in the room is illustrated in FIG. 3.

Curve A represents the control value at 70.6 µg/m$^3$, without an air purifier of the invention.

Curve B represents the change in the concentration when the air purifier of the invention is in operation.

It can thus be noted that after a few hours of operation, the formaldehyde release rate drops below 20 µg/m$^3$ (lower than the 30 µg/m$^3$ rate recommended in establishments open to the public).

The second example is defined for achieving the decontamination of a room having the same features as in the previous example, but with the following features of the air purifier using the filter cartridge of the invention:
air flow: 70 m$^3$/h,
alveolar (honeycomb) filter cartridge: width 24 cm, length 29 cm, depth 1 cm (total passage surface area of 0.042 m$^2$),
weight of the specific absorbent material: 10 g.

Figure 4:
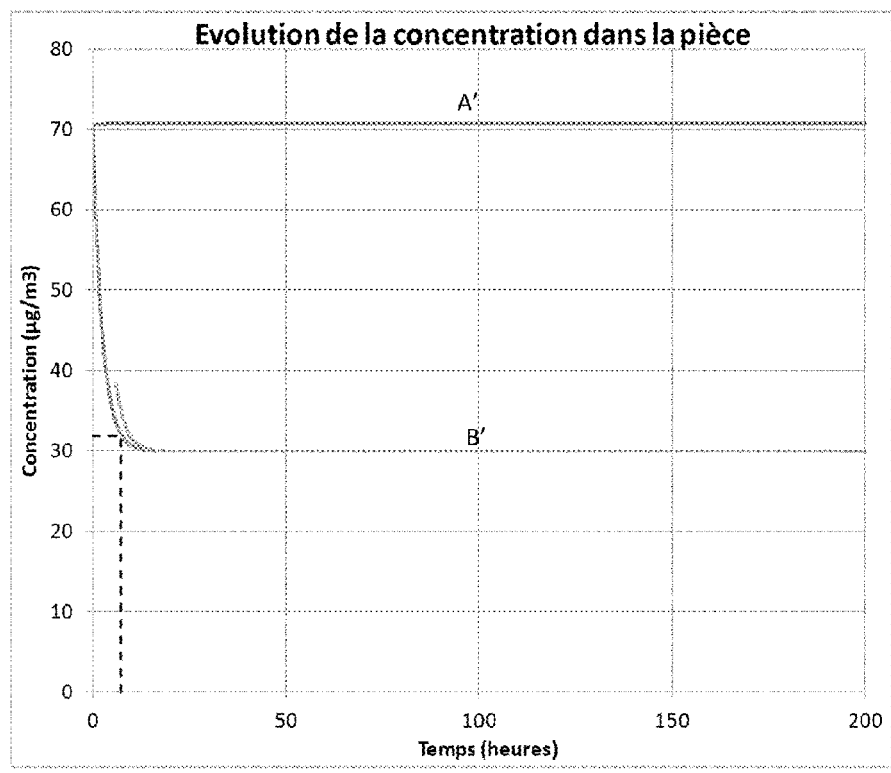
FIG. 4 illustrates the change in the concentration of formaldehyde in a room with a second alternative embodiment of the cartridge of the invention.

The change in the concentration of formaldehyde in the room is illustrated in FIG. 4.

Curve A' represents the control value at 70.6 µg/m$^3$, without an air purifier of the invention.

Curve B' represents the change in the concentration when the air purifier of the invention is in operation.

It can thus be noted that after a few hours of operation, the formaldehyde release rate is around 30 µg/m$^3$.

It is understood that diverse modifications and/or improvements obvious to a person skilled in the art may be made to the embodiments of the invention described in the present description without exceeding the scope of the invention defined by the appended claims.

The two exemplary embodiments were thus given for an air purifier for domestic use (room a few m$^3$ in volume). Applications of filter cartridges of the invention in a larger air purifier (for example, one designed for an establishment open to the public) are conceivable. It suffices to use either more cartridges or cartridges with larger dimensions.

The invention claimed is:

1. Filter cartridge for an air purifier comprising a structure ensuring the retention of a filter medium, the filter medium comprising a standard absorbent material chosen from the group consisting of activated charcoal or zeolites, wherein the filter medium further comprises a nanoporous specific absorbent material functionalized with probe molecules in such a way that aldehyde chemical pollutants can be trapped.

2. Filter cartridge for an air purifier as in claim 1, wherein the specific absorbent material is manufactured by sol-gel for incorporation in a nanoporous structure of metal oxides of probe molecules capable of trapping aldehydes.

3. Filter cartridge for an air purifier as in claim 1, wherein the probe molecule bearing a functional group capable of reacting with an aldehyde group is chosen from the group consisting of enaminones and corresponding β-diketone/amine pairs, imines, and hydrazines, or salts derived from these compounds.

4. Filter cartridge for an air purifier as in claim 1, wherein the structure ensuring the retention of the filter medium is a rigid alveolar structure, the alveoli containing the filter medium.

5. Filter cartridge for an air purifier as in claim 1, wherein a micro-perforated film is assembled on the upstream and downstream faces of the rigid alveolar structure.

6. Filter cartridge for an air purifier as in claim 4, wherein a filling rate of the alveoli with filter medium is greater than 40%.

7. Filter cartridge for an air purifier as in claim 1, wherein the specific absorbent material is in the form of granules with dimensions ranging between 0.8 and 2 mm.

8. Filter cartridge for an air purifier as in claim 7, wherein the shape of the granules is cylindrical with a ratio L/D>1, wherein L corresponds to a length of a granule and D corresponds to a diameter of a granule.

9. Filter cartridge for an air purifier as in claim 1, wherein the structure ensuring the retention of the filter medium is an assembly of several films on which the standard absorbent material and the specific absorbent material are impregnated/sprinkled.

10. Filter cartridge for an air purifier as in claim 1, wherein the weight of the specific absorbent material represents between 5 and 95% of the weight of the standard absorbent material.

11. Filter cartridge for an air purifier as in claim 1, wherein the specific surface area of the specific absorbent material ranges between 600 and 1200 $m^2g$.

12. Air purifier, comprising at least one filter cartridge defined according to claim 1.

13. Filter cartridge for an air purifier as in claim 2, wherein the structure ensuring the retention of the filter medium is an assembly of several films on which the standard absorbent material and the specific absorbent material are impregnated/sprinkled.

14. Filter cartridge for an air purifier as in claim 3, wherein the structure ensuring the retention of the filter medium is an assembly of several films on which the standard absorbent material and the specific absorbent material are impregnated/sprinkled.

* * * * *